United States Patent
Toti et al.

(10) Patent No.: US 10,251,891 B2
(45) Date of Patent: Apr. 9, 2019

(54) APREPITANT ORAL LIQUID FORMULATIONS

(71) Applicant: InnoPharma, Inc., New York, NY (US)

(72) Inventors: Udaya Toti, Monmouth Junction, NJ (US); Shyamprasad Mukundan, Parsippany, NJ (US); Sasank Chaitanya Kunadharaju, Edison, NJ (US); Tushar Hingorani, Piscataway, NJ (US); Kumaresh Soppimath, Monmouth Junction, NJ (US); Satish Pejaver, Bridgewater, NJ (US); Navneet Puri, Bridgewater, NJ (US)

(73) Assignee: InnoPharma, Inc., Piscataway, NJ (US)

( * ) Notice: Subject to any disclaimer, the term of this patent is extended or adjusted under 35 U.S.C. 154(b) by 0 days.

(21) Appl. No.: 15/333,529

(22) Filed: Oct. 25, 2016

(65) Prior Publication Data

US 2017/0035774 A1    Feb. 9, 2017

Related U.S. Application Data

(63) Continuation of application No. 14/509,964, filed on Oct. 8, 2014, now abandoned.

(51) Int. Cl.

| | |
|---|---|
| *A61K 31/5377* | (2006.01) |
| *A61K 9/00* | (2006.01) |
| *A61K 47/12* | (2006.01) |
| *A61K 9/10* | (2006.01) |
| *A61K 47/38* | (2006.01) |
| *A61K 47/20* | (2006.01) |
| *A61K 9/14* | (2006.01) |

(52) U.S. Cl.
CPC ........ *A61K 31/5377* (2013.01); *A61K 9/0053* (2013.01); *A61K 9/0095* (2013.01); *A61K 9/10* (2013.01); *A61K 47/12* (2013.01); *A61K 47/20* (2013.01); *A61K 47/38* (2013.01); *A61K 9/146* (2013.01)

(58) Field of Classification Search
CPC .. A61K 31/5377; A61K 9/0053; A61K 47/12; A61K 9/0095; A61K 47/38
See application file for complete search history.

(56) References Cited

U.S. PATENT DOCUMENTS

| | | | |
|---|---|---|---|
| 2004/0105889 A1* | 6/2004 | Ryde | A61K 9/0095 424/489 |
| 2004/0214746 A1* | 10/2004 | Bosch | A61K 9/145 514/1 |
| 2009/0209541 A1 | 8/2009 | Jain et al. | |
| 2011/0009362 A1 | 1/2011 | Joshi et al. | |
| 2011/0015191 A1 | 1/2011 | Ludescher et al. | |
| 2013/0209521 A1 | 8/2013 | Filipcsei et al. | |
| 2013/0317016 A1* | 11/2013 | Hingorani | A61K 31/5377 514/230.8 |
| 2014/0272100 A1 | 9/2014 | Samburski et al. | |

FOREIGN PATENT DOCUMENTS

| | | |
|---|---|---|
| WO | 2007044829 A2 | 4/2007 |
| WO | 2007147160 A2 | 12/2007 |
| WO | 2008104512 A2 | 9/2008 |
| WO | 2009108828 A2 | 9/2009 |
| WO | 2011158053 A1 | 12/2011 |
| WO | 2012085071 A1 | 6/2012 |
| WO | 2013177501 A2 | 11/2013 |
| WO | 2014005606 A1 | 1/2014 |

OTHER PUBLICATIONS

Singh, S.K., et al., "Investigation of Preparation Parameters of Nanosuspension by Top-Down Media Milling to Improve the Dissolution of Poorly Water-Soluble Glyburide," European Journal of Pharmaceutics and Biopharmaceutics, vol. 78 (2011) 441-446.

Olver, I., et al., "Nanomedicines in the treatment of emesis during chemotherapy: focus on aprepitant," International Journal of Nanomedicine 2007:2(1) 13-18.

ISA/KR, International Search Report and Written Opinion, Int'l Appln No. PCT/US2014/059767, dated Jan. 30, 2015 (9 pages).

\* cited by examiner

*Primary Examiner* — Mina Haghighatian
(74) *Attorney, Agent, or Firm* — Jason G. Tebbutt

(57) ABSTRACT

A liquid pharmaceutical compositions comprising Aprepitant is preferably prepared as an oral suspension dosage form for the prevention and control of acute and delayed chemotherapy induced nausea and vomiting, and/or for prevention of postoperative nausea and vomiting.

20 Claims, No Drawings

APREPITANT ORAL LIQUID
FORMULATIONS

This application is a continuation application of U.S. patent application Ser. No. 14/509,964, filed Oct. 8, 2014, which claims the benefit of U.S. Provisional Patent Application No. 61/888,092, filed on Oct. 8, 2013, the disclosures of which are hereby incorporated by reference in their entirety.

FIELD OF THE INVENTION

The field of the invention is liquid pharmaceutical compositions comprising aprepitant, especially as oral suspension dosage forms for the prevention and control of acute and delayed chemotherapy induced nausea and vomiting, and/or for prevention of postoperative nausea and vomiting.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

Aprepitant (5-([(2R,3S)-2-((R)-1-[3,5-bis(trifluoromethyl)phenyl]ethoxy)-3-(4-fluoro-phenyl)morpholino]methyl)-1H-1,2,4-triazol-3(2H)-one) is an antiemetic compound that belongs to the class of substance P antagonists that mediate their effect by blocking the neurokinin (NK1) receptor. Aprepitant is a selective, high-affinity antagonist at human substance P NK-1 receptors and is manufactured by Merck & Co. (available under the brand name, Emend®). It is available as solid capsules (40, 80 and 125 mg) or powder (115 and 150 mg) for injection for the prevention and control of acute and delayed chemotherapy induced nausea and vomiting, and for prevention of postoperative nausea and vomiting. The recommended dose of EMEND capsules is 125 mg orally 1 hour prior to chemotherapy treatment (Day 1) and 80 mg orally once daily in the morning on Days 2 and 3 and also indicated for the postoperative nausea and vomiting (PONV) 40 mg within 3 hours prior to induction of anesthesia.

Following oral administration of a single 40 mg dose of EMEND in the fasted state, mean area under the plasma concentration-time curve (AUCo-∞) was 7.8 mcg/hr/mL and mean peak plasma concentration (Cmax) was 0.7 mcg mL, occurring at approximately 3 hours post-dose (tmax). The absolute bioavailability at the 40-mg dose has not been determined. Following oral administration of a single 125-mg dose of EMEND on Day 1 and 80 mg once daily on Days 2 and 3, the AUCo-24 hr was approximately 19.6 mcg*hr/mL and 21.2 mcg*hr/mL on Day 1 and Day 3, respectively. The Cmax of 1.6 mcg mL and 1.4 mcg/mL were reached in approximately 4 hours (Tmax) on Day 1 and Day 3, respectively. At the dose range of 80-125 mg, the mean absolute oral bioavailability of aprepitant is approximately 60 to 65%.

Unfortunately, oral capsule formulations may not be easy to swallow for patients after chemotherapy or postoperative condition as such capsules often induce nausea and vomiting, and there are no liquid formulation of aprepitant commercially available. In an alternative described elsewhere (Secundum Artem; Current & Practical Compounding Information for the Pharmacist. Perrigo Pharmaceuticals (Volume 16 Number 1)), an aprepitant oral suspension can be prepared at the point of use by grinding a 125 mg capsule and combining the ground powder with Ora-Blend™ (gum-based fluid, commercially available from Paddock laboratories). Here, contents of an aprepitant capsule were emptied into a mortar and ground to a fine powder. A small amount of Ora-Blend® was added to the fine powder and triturated to a smooth paste. More Ora-Blend was added and the mixture transferred to a graduate. The mortar was rinsed with Ora-Blend and the mixture added to the graduate. Finally, sufficient Ora-Blend was added to final volume and mixed well. Unfortunately, such preparations are not stable and will generally not achieve a uniform suspension, which may affect bioavailability.

Such and other difficulties in preparing aprepitant solutions are well known in the art and are described, for example, in US 2009/0209541 and US 2011/0009362, particularly as they relate to solubility of aprepitant. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, WO 03/049718 addresses various issues associated with poor delivery characteristics of aprepitant. Here, nanoparticulate compositions of aprepitant are disclosed with stabilizers adsorbed on its surface to maintain an effective average particle size of less than about 1000 nm. On the other hand, US 2014/0272100 teaches coatings of carrier particles with aprepitant microparticles, and WO 2008/104512 describes different polymorphs in an attempt to increase solubility. However, all or almost all of compositions fail to provide a premade liquid formulation that is stable over a prolonged time, particularly where suspensions are prepared. Among other difficulties, the particles in the suspensions tend to agglomerate over time and precipitate out of solution and/or become less bioavailable due to increase in size.

Therefore, even though numerous liquid formulations for aprepitant are known in the art, all or almost all of them suffer from one or more disadvantage. Thus, there is still a need to provide improved oral liquid aprepitant formulations that have aprepitant particles in suspension for extended time without agglomeration and concomitant precipitation.

SUMMARY OF THE INVENTION

The inventive subject matter is directed to compositions and methods for stabilized aqueous suspension of aprepitant particles for oral administration in which aprepitant is provided in a suspension having a cellulosic stabilizer and an anionic surfactant in amounts sufficient to limit growth of the aprepitant particles.

In one aspect of the inventive subject matter, the inventors contemplate a method of producing a stabilized aqueous suspension of aprepitant for oral administration. In especially preferred methods, a pharmaceutically effective amount of aprepitant particles, a cellulosic stabilizer, and an anionic surfactant are combined with an acidic aqueous buffer to form a stabilized aqueous suspension. Most typically, the aprepitant particles have an average particle size of less than 0.5 micron, and the cellulosic stabilizer and the anionic surfactant are present in an amount that limits growth of the aprepitant particles in the stabilized aqueous suspension to equal or less than 20% within a month at ambient conditions. The so prepared stabilized aqueous suspension is then packaged in a form that is suitable for oral administration.

In further contemplated aspects, the aprepitant particles have an average particle size of less than 0.4 micron, and/or aprepitant is present in the stabilized aqueous suspension in an amount of between 10.0 mg/g and 20.0 mg/g. Most typically, the acidic aqueous buffer has a pH of between 3.0 and 5.0. Moreover, it is preferred that the cellulosic stabilizer comprises a substituted cellulose (e.g., hydroxypropyl methylcellulose) and is present in the stabilized aqueous suspension in an amount of between 2.0 mg/g and 10.0 mg/g. With respect to the anionic surfactant it is generally preferred that the anionic surfactant is an alkylsulfate (e.g., sodium docecylsulfate) and is present in the stabilized aqueous suspension in an amount of between 0.5 mg/g and 5.0 mg/g.

Therefore, it is contemplated in certain aspects that the cellulosic stabilizer comprises a substituted cellulose that is present in the stabilized aqueous suspension in an amount of between 2.0 mg/g and 10.0 mg/g, and that the anionic surfactant is an alkylsulfate that is present in the stabilized aqueous suspension in an amount of between 0.5 mg/g and 5.0 mg/g. For example, contemplated aspects will include stabilized aqueous suspension where the cellulosic stabilizer is hydroxypropyl methylcellulose (especially having a viscosity grade of E3 to E15, translating to a viscosity of 2.4 Cps to 18 Cps of a 2.0% solution of the polymer) and is present in the stabilized aqueous suspension in an amount of between 4.0 mg/g and 8.0 mg/g, while the anionic surfactant is sodium docecylsulfate and is present in the stabilized aqueous suspension in an amount of between 1.0 mg/g and 4.0 mg/g.

Consequently, the inventors also contemplate a stabilized aqueous suspension of aprepitant for oral administration that includes a pharmaceutically effective amount of aprepitant particles (e.g., having an average particle size of less than 0.5 micron), an acidic aqueous buffer, and a cellulosic stabilizer and an anionic surfactant in an amount effective that limits growth of the aprepitant particles to equal or less than 20% within a month at ambient conditions. Most preferably, the aqueous suspension of aprepitant is formulated for oral administration and packaged into a container for use (e.g., single use container containing between 5 and 15 ml of the stabilized aqueous suspension).

It is generally preferred that the aprepitant is present in the stabilized aqueous suspension in an amount of between 10.0 mg/g and 20.0 mg/g, and/or that the acidic aqueous buffer is a citrate buffer. As noted above, it is contemplated that the cellulosic stabilizer comprises a substituted cellulose (e.g., hydroxypropyl methylcellulose), and that the cellulosic stabilizer is present in the stabilized aqueous suspension in an amount of between 2.0 mg/g and 10.0 mg/g. Likewise, it is contemplated that the anionic surfactant is an alkylsulfate (e.g., sodium docecylsulfate), and that the anionic surfactant is present in the stabilized aqueous suspension in an amount of between 0.5 mg/g and 5.0 mg/g. Therefore, contemplated stabilized aqueous suspensions include those in which the cellulosic stabilizer comprises a substituted cellulose that is present in the stabilized aqueous suspension in an amount of between 2.0 mg/g and 10.0 mg/g, and in which the anionic surfactant is an alkylsulfate that is present in the stabilized aqueous suspension in an amount of between 0.5 mg/g and 5.0 mg/g. For example, suitable stabilized aqueous suspension will include those in which the cellulosic stabilizer is hydroxypropyl methylcellulose and present in an amount of between 4.0 mg/g and 8.0 mg/g, and in which the anionic surfactant is sodium docecylsulfate and is present in an amount of between 1.0 mg/g and 4.0 mg/g.

Various objects, features, aspects and advantages of the inventive subject matter will become more apparent from the following detailed description of preferred embodiments.

DETAILED DESCRIPTION

The inventors discovered that various stable pharmaceutical liquid formulations for oral administration of aprepitant can be prepared that maintain aprepitant particles in suspension over extended periods of time. For example, exemplary formulations will include aprepitant particles having an average particle size of less than 0.5 or less than 0.4 micron in combination with one or more cellulosic stabilizer and anionic surfactant (preferably at an acidic pH using a buffer). Such formulations are typically stable at ambient conditions (25° C., 60% relative humidity) for at least one month while limiting growth of aprepitant particles to equal or less than 20%. Such solutions are typically packaged in single use containers at a volume to provide a desired (e.g., 40 mg, 80 mg, 125 mg, etc.) quantity of aprepitant to a patient in need thereof. Most typically, such formulations are administered to the patient to prevent nausea and vomiting upon or after chemotherapy treatment for cancer and/or to prevent post-operative nausea and vomiting.

Thus, one aspect of the inventive subject matter is directed to compositions and methods of formulating a stable pharmaceutical oral liquid formulation that comprises aprepitant and one or more pharmaceutically acceptable excipients in a single or multiple dosage form. Viewed from a different perspective, compositions and methods for stable pharmaceutical oral liquid formulation comprising of aprepitant are contemplated where aprepitant is present in the formulation at a concentration of 40-125 mg/ml and a fill volume from 5-25 ml per container. As used herein, the term "pharmaceutically acceptable" means biologically or pharmacologically compatible for in-vivo use in animals or humans, and can mean approved by a regulatory agency of the Federal or a state government or listed in the U.S. Pharmacopeia or other generally recognized pharmacopeia for use in animals, and more particularly in humans. Contemplated compositions and methods provide stable pharmaceutical oral liquid formulations comprising aprepitant and pharmaceutically acceptable excipients in which the formulation is a ready to use suspension of aprepitant nanoparticles. Such nanoparticles will typically have an average particle size of between 0.050 and 1000 microns. For example, suitable sizes include those between 0.050 and 0.100 microns, between 0.100 and 0.500 microns, between 0.500 and 0.700 microns, or between 0.700 and 1.000 microns. Of course, it should be appreciated that compositions and methods contemplated herein also include additional agents to enhance one or more desirable properties, including flavor and palatability. Thus contemplated formulations may also include preservatives, coloring agents, and/or flavoring agents. Most preferably, the stable pharmaceutical oral liquid formulation contemplated herein has pharmacokinetic parameters that are comparable to that of the pharmacokinetic parameters after administration of oral capsules.

In one exemplary aspect of the inventive subject matter, contemplated formulations are palatable, oral ready-to-use formulations of aprepitant (i.e., do not require dilution, mixing with other solvents, or further manipulation that change the composition). It should be particularly appreciated that aprepitant has been used in parenteral and solid oral medicinal products, but has not previously been used in oral liquid preparations that were stable over extended periods and that could be retrieved from the packing in a ready to use form.

Aprepitant is practically insoluble in water, and the low solubility presents a formulary challenge during product development of an aqueous liquid oral preparation. Moreover, it should be recognized that the particle size of the active pharmaceutical ingredient may have important effects on the bioavailability of a formulation. Smaller particle sizes often have increased surface area and will thus dissolve faster than larger particles. However, decreasing the particle size will often increase agglomeration of the particles, and an increased surface area of smaller particles can result in faster degradation of the compound, e.g., due to oxidation and/or hydrolysis. The inventors have now found out that a fine particle size, and especially an average particle size between 0.250 and 0.400 micron, could achieve a desirable bioavailability (typically identical to that of commercially available solid oral aprepitant, EMEND). Such particle size may preferably be achieved using air-jet milling, ball milling, or mortar milling. When such particle size was used in conjunction with an aqueous suspension having cellulosic stabilizer as a surface coating and/or dispersing and/or thickening agent and an anionic surfactant, contemplated formulations exhibited remarkable stability against agglomeration (e.g., increase of average particle size) while maintaining desired pharmacokinetic parameters. Indeed, it was observed that aprepitant was and remained evenly dispersed in the thickened aqueous vehicle and had a homogeneity so that the aprepitant was uniformly present but undissolved in the formulation for extended periods (e.g., at least one month, or two months, or three months at ambient conditions).

For example, the inventors produced a stabilized aqueous suspension of aprepitant for oral administration by combining a pharmaceutically effective amount of aprepitant particles, a cellulosic stabilizer, and an anionic surfactant with an acidic aqueous buffer to form a stabilized aqueous suspension. In such method, the average particle size was less than 0.5 micron, and in most cases between 0.200 and 0.400 micron (e.g., 0.300+/−50 micron), and the so prepared stabilized aqueous suspension had a stability (i.e., particle growth less than 20 absolute) of over 1 month at ambient conditions. In particularly preferred aspects, aprepitant was present between 10.0 mg/g and 20.0 mg/g (e.g., 15+/−10%) of the stabilized aqueous suspension, while the acidic aqueous buffer has a pH of between 3.0 and 5.0 (e.g., citrate buffer).

Preferred cellulosic stabilizers will act as a thickening agent, and especially preferred were hydroxypropyl methylcellulose that was included in a range of between 2.0 mg/g and 10.0 mg/g or between 4.0 mg/g and 8.0 mg/g (e.g., 6+/−1 mg/g). Likewise, preferred anionic surfactants were alkylsulfates, and especially sodium docecylsulfate that was included in a range of between 0.5 mg/g and 5.0 mg/g or between 1.0 mg/g and 4.0 mg/g (e.g., 1.5+/−0.5 mg/g). Such formulations provided superior stability and had desirable pharmacokinetic parameters. Thus, preferred stabilized aqueous suspension of aprepitant for oral administration will include a pharmaceutically effective amount of aprepitant particles, wherein the aprepitant has an average particle size of less than 0.5 micron. Contemplated suspensions will further include a cellulosic stabilizer and an anionic surfactant in an amount effective that limits growth of the aprepitant particles to equal or less than 20% within a month at ambient conditions, and also include an acidic aqueous buffer, and wherein the aqueous suspension of aprepitant is formulated for oral administration. Of course, it should be recognized that contemplated suspensions may comprise at least one additional component selected from the group consisting of sweetening agents, flavoring agents, coloring agents, preservatives, oily vehicles, solvents, suspending agents, dispersing agents, antioxidants, permeation enhancing agents, oral bioavailability enhancing agents, and stabilizing agents.

With respect to suitable surfactants it is contemplated that various surfactants may be used in conjunction with the teachings herein and exemplary surfactants include various anionic surfactants, and to a lesser degree also nonionic and amphoteric surfactants. Especially suitable anionic surfactants include water-soluble salts of $C_{8-20}$ alkyl sulfates, sulfonated monoglycerides of $C_{8-20}$ fatty acids, sarcosinates, taurates, and mixtures thereof. Illustrative examples of these and other surfactants are sodium lauryl sulfate, sodium coconut monoglyceride sulfonate, sodium lauryl sarcosinate, sodium lauryl isoethionate, sodium laureth carboxylate and sodium dodecyl benzenesulfonate, dioctyl sodium sulfosuccinate and mixtures thereof. Suitable nonionic surfactants include xpoloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. Suitable amphoteric surfactants include derivatives of $C_{8-20}$ aliphatic secondary and tertiary amines having an anionic group such as carboxylate, sulfate, sulfonate, phosphate or phosphonate. A suitable example is cocoamidopropylbetaine. One or more surfactants are optionally present in a total amount of about 0.01% to about 10%.

Likewise, numerous stabilizing agents acting as thickeners are also deemed suitable and include tragacanth, xanthan gum, bentonite, starch, acacia, and/or lower alkyl ethers of cellulose (including the hydroxy and carboxy derivatives of the cellulose ethers). Examples of celluloses include, e.g., hydroxypropyl cellulose, hydroxypropyl methyl cellulose, sodium carboxy methylcellulose, microcrystalline cellulose (MCC), and MCC with sodium carboxyl methyl cellulose. In liquid formulations, such thickening agents may also function as suspending agents which can be used alone or in combinations. Exemplary suspending agents may include starch instant clearjel and xanthan gum. Starch instant clearjel may be used in the amount of from about 0.1 to about 10% w/v and preferably about 2 to about 3% w/v. Xanthan gum is used in the amount of from about 0.01 to about 5% w/v and preferably about 0.1-0.3% w/v. For solid formulations, particularly desirable bulking agents include mannitol and microcrystalline cellulose.

Further contemplated stabilizers include hypromellose that is ordinarily used as an excipient (coating and/or dispersing agent) in oral tablet and capsule formulations, where, depending on the grade, it functions as controlled release agent to delay the release of a medicinal compound into the digestive tract. Hypromellose is also used as a binder and as a component of tablet coatings, and notably form in solution non-Newtonian fluids and increases viscosity. Suitable suspending agents for use in the aqueous suspensions according to the present invention are cellulose derivatives, e.g. methyl cellulose, sodium carboxymethyl cellulose and hydroxypropyl methyl cellulose, alginates, gelatin, chitosan, dextrans, polyvinylpyrrolidone, polyethylene glycols, polyoxyethylene- and polyoxypropylene ethers. While numerous polymer forms/lengths of hypromellose are known in the art, especially preferred forms of hypromellose include those having a viscosity grade of E3 to E15, which translates to a viscosity of 2.4 Cps to 18 Cps of a 2.0% solution of the polymer.

Further contemplated agents include bulking agents that are known in the art. Bulking agents may be used alone or in combination in an amount of about 5% w/w to a total amount of up to about 90% w/w, preferably about 10% w/w to a total amount of up to about 70% w/w, more preferably about 10% w/w to about 50% w/w, most preferably about 10% to about 30% w/w. In one embodiment, mannitol and/or microcrystalline cellulose may be used in an amount of about 10% w/w to about 15% w/w. When used in combination, they may be present in a ratio of 1:1 w/v or one more be present in a higher amount than another.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include methol, menthyl acetate, menthyl lactate, camphor, eucalyptus oil, eucalyptol, anethole, eugenol, cassia, oxanone, .alpha.-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5%, optionally from about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof. In addition, contemplated compositions and formulations will also include one or more preservative agents and exemplary agents include ethyl alcohol, propylene glycol, glycerin, benzyl alcohol, benzoic acid, sodium benzoate, potassium benzoate, asorbic acid, potassium sorbate, esters of p-hydroxybenzoic acid (parabens), benzalkonium chloride solution NF, and especially sodium benzoate. Suitable quantities of such preservative agents will generally follow those well known in the art.

Most typically, contemplated stabilized aqueous suspension of aprepitant for oral administration will be packaged in a sterile single use container that contains a unit dose for administration to a patient. Thus, suitable containers may contain volumes of between 1-10 ml, 10-20 ml, 20-40 ml, and 40-100 ml, and even more. Viewed from a different perspective, the container will typically comprise aprepitant in an amount of between 20-40 mg, between 40-80 mg, between 80-130 mg, or even more. Thus, while not preferred, it should also be noted that the container may be a multi-use container (i.e., retains at least one more unit dose after a first unit dose is dispensed).

EXAMPLES

The following examples do not limit the scope of applicant's invention but serve as an explanatory tool of applicant's invention. The inventors have tested various methods and these methods may be conceptually grouped into different classes. Examples 1 and 2 were draw to solutions of aprepitant in which an attempt was made to solubilize the active ingredient using non-aqueous solvents and emulsifiers as shown in the examples of Tables 1 and 2.

TABLE 1

| Example 1 | Aprepitant Solution |
| --- | --- |
| Aprepitant | 125 mg |
| Ethanol | 10 mL |
| Polysorbate 80 | 500 mg |
| Water | 10 mL |
| Flavoring Agent | Required quantity |
| Sweetening agent | Required quantity |

TABLE 2

| Example 2 | Aprepitant Solution |
| --- | --- |
| Aprepitant | 80 mg |
| Ethanol | 5 mL |
| Polysorbate 80 | 500 mg |
| Water | 5 mL |
| Flavoring Agent | Required quantity |
| Sweetening agent | Required quantity |

In both of the listed examples, stability for aprepitant in solution was not achieved and the aprepitant precipitated out of solution in relatively short time. In an attempt to remedy the lack of stability, the inventors formulated non-micronized aprepitant with low concentrations of a surfactant and various stabilizer, which also produced unsatisfactory results as the aprepitant precipitated out of solution in relatively short time. Exemplary formulations are shown in the examples of Tables 3 and 4 below.

TABLE 3

| Example 3 | Aprepitant Suspension |
| --- | --- |
| Aprepitant | 125 mg |
| Sodium lauryl sulphate | 100 mg |
| Sodium CMC | 50 mg |
| Water | 5 mL |
| Flavoring Agent | Required quantity |
| Sweetening agent | Required quantity |

TABLE 4

| Example 4 | Aprepitant Suspension |
| --- | --- |
| Aprepitant | 80 mg |
| Sodium lauryl sulphate | 75 mg |
| Xanthan Gum | 25 mg |
| Water | 5 mL |
| Flavoring Agent | Required quantity |
| Sweetening agent | Required quantity |

The inventors then attempted to formulate aprepitant with a co-solvent as exemplarily described in the examples of Tables 5-8. Once more, aprepitant precipitated out of solution in relatively short time.

TABLE 5

| Example 5 | Partially soluble Aprepitant suspension |
| --- | --- |
| Aprepitant | 125 mg |
| Ethanol | 2 mL |
| Gelucire 44/14 | 180 mg |
| Water | 3 mL |
| Flavoring Agent | Required quantity |
| Sweetening agent | Required quantity |

TABLE 6

| Example 6 | Partially soluble Aprepitant suspension |
| --- | --- |
| Aprepitant | 80 mg |
| Ethanol | 2 mL |
| Sodium lauryl sulphate | 80 mg |
| Water | 3 mL |
| Flavoring Agent | Required quantity |
| Sweetening agent | Required quantity |

TABLE 7

| Example 7 | Partially soluble Aprepitant suspension |
| --- | --- |
| Aprepitant | 125 mg |
| Ethanol | 2 mL |

TABLE 7-continued

| Example 7 | Partially soluble Aprepitant suspension |
| --- | --- |
| Vitamin E TPGS | 100 mg |
| Water | 3 mL |
| Flavoring Agent | Required quantity |
| Sweetening agent | Required quantity |

TABLE 8

| Example 8 | Partially soluble Aprepitant suspension |
| --- | --- |
| Aprepitant | 80 mg |
| Ethanol | 2 mL |
| Vitamin E TPGS | 80 mg |
| Water | 3 mL |
| Flavoring Agent | Required quantity |
| Sweetening agent | Required quantity |

The inventors then investigated micronized aprepitant at various particle sizes (some data not shown) and unexpectedly discovered that micronized aprepitant when in combination with a cellulosic stabilizer (acting as a coating and/or dispersing agent) and an anionic surfactant formed suspensions that were stable over extended periods at ambient (20-25° C., 60% RH) storage conditions. Exemplary compositions and associated stability data are shown in Tables 9-10 below. Notably, addition of PVA (known as a stabilizer for various compounds) was not a determinative factor for stability for aprepitant, and use of a branched-chain surfactant with carbonyl groups appeared to abrogate stability for otherwise similar compositions.

Slurry Phase Preparation: Take purified water, approximately 5% of the target batch weight. Add and dissolve Sodium lauryl sulphate, NF, approximately 8% of the required batch quantity, Sodium benzoate, NF, 100% of the required batch quantity, Sodium citrate dihydrate, USP, 40% of the required batch quantity, Citric acid monohydrate, USP, 3.5% of the required batch quantity, Benecel E5 Pharm hypromellose, 100% of the required batch quantity. Add calculated amount of Aprepitant to the vessel under stirring over the time period of 30 minutes and stir until contents are completely dispersed. Q.S. with Purified water to approximately 8% of the batch weight and stir for NLT 15 minute and ensure there is no visible lump.

Diluent Phase Preparation: Take purified water, approximately 60% of the target batch weight. Add and dissolve the remaining Sodium lauryl sulphate, NF, Sodium citrate dihydrate, USP, Citric acid monohydrate, USP. Add and dissolve the required quantity of Sucrose, USP. Q.S. to about 70.0% of the target batch weight.

Nano-Milling and preparation of final formulation: Set up the nanomill with 270 mL zirconium beads (Bead size: 0.3 mm to 4.0 mm). Add slurry phase to nanomill feeding vessel. Run nanomill with set parameters: pump speed and mill agitator speed. Measure the particle size distribution on the in-process samples and continue milling until the target particle size is reached. Collect the milled slurry in a vessel. Rinse the nanomill with the diluent phase. Collect the rinse in the same vessel as that containing the milled slurry. Q.S the batch to the required weight.

TABLE 9

| Ingredients | Example 9 (mg/g) | Example 10 (mg/g) | Example 11 (mg/g) | Example 12 (mg/g) | Example 13 (mg/g) |
|---|---|---|---|---|---|
| Aprepitant, USP | 15.625 | 15.625 | 15.625 | 16.000 | 16.000 |
| Benecel E5 Pharm hypromellose | 6.000 | 6.000 | 6.000 | 6.000 | 6.000 |
| Polyvinyl alcohol, USP | —/— | —/— | 2.500 | 2.500 | —/— |
| Docusate sodium USP/NF | —/— | —/— | —/— | 1.150 | 1.150 |
| Sodium lauryl sulphate, NF | 1.500 | 3.000 | 3.000 | —/— | —/— |
| Sodium benzoate, NF | 1.826 | 1.826 | 1.826 | 1.826 | 1.826 |
| Sodium citrate dihydrate, USP | 0.091 | 0.091 | 0.091 | 0.091 | 0.091 |
| Citric acid monohydrate, USP | 1.369 | 1.369 | 1.369 | 1.369 | 1.369 |
| Sucrose, USP | 50.00 | 50.00 | 50.00 | 50.00 | 50.00 |
| Purified Water | q.s. to 1000 | q.s. to 1000 | q.s. to 1000 | q.s. to 1000 | q.s. to 1000 |

TABLE 10

| | PARTICLE SIZE (μm) | | |
|---|---|---|---|
| EXAMPLE | Initial | Stability Condition 20° C. to 25° C. Day-7 | Stability Condition 25° C. ± 2° C./60% RH ± 5% 1 Month |
| Example 9 | 0.302 | n/d | 0.350 |
| Example 10 | 0.303 | n/d | 0.358 |
| Example 11 | 0.309 | n/d | 0.345 |
| Example 12 | 0.322 | 1.202 | n/d |
| Example 13 | 0.323 | 95.888 | n/d |

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise.

What is claimed is:

1. A method of producing a stabilized, ready-to-use, aqueous suspension of aprepitant for oral administration, the method comprising:

combining a pharmaceutically effective amount of aprepitant particles, a cellulosic stabilizer, and an anionic surfactant with an acidic aqueous buffer to form a stabilized aqueous suspension;

wherein the aprepitant particles have an average particle size of less than 0.5 micron;

wherein the cellulosic stabilizer and the anionic surfactant are present in an amount effective that limits growth of the aprepitant particles in the stabilized aqueous suspension to equal or less than 20% within a month at ambient conditions; and packaging the stabilized aqueous suspension in a ready-to-use form suitable for oral administration.

2. The method of claim 1 wherein the aprepitant particles have an average particle size of less than 0.4 micron.

3. The method of claim 1 wherein the aprepitant is present in the stabilized aqueous suspension in an amount of between 10.0 mg/g and 20.0 mg/g.

4. The method of claim 1 wherein the acidic aqueous buffer has a pH of between 3.0 to 5.0.

5. The method of claim 1 wherein the cellulosic stabilizer comprises a substituted cellulose, and wherein the cellulosic stabilizer is present in the stabilized aqueous suspension in an amount of between 2.0 mg/g and 10.0 mg/g.

6. The method of claim 5 wherein the cellulosic stabilizer is hydroxypropyl methylcellulose.

7. The method of claim 1 wherein the anionic surfactant is an alkylsulfate, and wherein the anionic surfactant is present in the stabilized aqueous suspension in an amount of between 0.5 mg/g and 5.0 mg/g.

8. The method of claim 7 wherein the anionic surfactant is sodium dodecylsulfate.

9. The method of claim 1 wherein the cellulosic stabilizer comprises a substituted cellulose that is present in the stabilized aqueous suspension in an amount of between 2.0 mg/g and 10.0 mg/g, and wherein the anionic surfactant is an alkylsulfate that is present in the stabilized aqueous suspension in an amount of between 0.5 mg/g and 5.0 mg/g.

10. The method of claim 1 wherein the cellulosic stabilizer is hydroxypropyl methylcellulose and is present in the stabilized aqueous suspension in an amount of between 4.0 mg/g and 8.0 mg/g, and wherein the anionic surfactant is sodium dodecylsulfate and is present in the stabilized aqueous suspension in an amount of between 1.0 mg/g and 4.0 mg/g.

11. A stabilized, ready-to-use, aqueous suspension of aprepitant for oral administration, comprising:
   a pharmaceutically effective amount of aprepitant particles, wherein the aprepitant has an average particle size of less than 0.5 micron;
   a cellulosic stabilizer and an anionic surfactant in an amount effective that limits growth of the aprepitant particles to equal or less than 20% within a month at ambient conditions;
   an acidic aqueous buffer, and wherein the ready-to-use aqueous suspension of aprepitant is formulated for oral administration.

12. The stabilized, ready-to-use, aqueous suspension of claim 11 wherein the aprepitant is present in the stabilized, ready-to-use, aqueous suspension in an amount of between 10.0 mg/g and 20.0 mg/g.

13. The stabilized, ready-to-use, aqueous suspension of claim 11 wherein the acidic aqueous buffer is a citrate buffer.

14. The stabilized, ready-to-use, aqueous suspension of claim 11 packaged in a single use container containing between 5 and 15 ml of the stabilized, ready-to-use, aqueous suspension.

15. The stabilized, ready-to-use, aqueous suspension of claim 11 wherein the cellulosic stabilizer comprises a substituted cellulose, and wherein the cellulosic stabilizer is present in the stabilized, ready-to-use, aqueous suspension in an amount of between 2.0 mg/g and 10.0 mg/g.

16. The stabilized, ready-to-use, aqueous suspension of claim 15 wherein the cellulosic stabilizer is hydroxypropyl methylcellulose.

17. The stabilized, ready-to-use, aqueous suspension of claim 11 wherein the anionic surfactant is an alkylsulfate, and wherein the anionic surfactant is present in the stabilized, ready-to-use, aqueous suspension in an amount of between 0.5 mg/g and 5.0 mg/g.

18. The stabilized, ready-to-use, aqueous suspension of claim 17 wherein the anionic surfactant is sodium dodecylsulfate.

19. The stabilized, ready-to-use, aqueous suspension of claim 11 wherein the cellulosic stabilizer comprises a substituted cellulose that is present in the stabilized aqueous suspension in an amount of between 2.0 mg/g and 10.0 mg/g, and wherein the anionic surfactant is an alkylsulfate that is present in the stabilized, ready-to-use, aqueous suspension in an amount of between 0.5 mg/g and 5.0 mg/g.

20. The stabilized, ready-to-use, aqueous suspension of claim 11 wherein the cellulosic stabilizer is hydroxypropyl methylcellulose and is present in the stabilized aqueous suspension in an amount of between 4.0 mg/g and 8.0 mg/g, and wherein the anionic surfactant is sodium dodecylsulfate and is present in the stabilized, ready-to-use, aqueous suspension in an amount of between 1.0 mg/g and 4.0 mg/g.

* * * * *